United States Patent
Boland et al.

(10) Patent No.: US 9,850,234 B2
(45) Date of Patent: *Dec. 26, 2017

(54) PYRIDINE DERIVATIVES AS SOFT ROCK INHIBITORS

(71) Applicant: Redx Pharma PLC, Greater Manchester (GB)

(72) Inventors: Sandro Boland, Diepenbeek (BE); Arnaud Bourin, Diepenbeek (BE); Olivier Defert, Diepenbeek (BE); Dirk Leysen, Diepenbeek (BE)

(73) Assignee: Redx Pharma PLC, Greater Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,219

(22) Filed: May 15, 2017

(65) Prior Publication Data

US 2017/0247357 A1 Aug. 31, 2017

Related U.S. Application Data

(63) Continuation of application No. 14/763,594, filed as application No. PCT/EP2014/051546 on Jan. 27, 2014, now Pat. No. 9,682,963.

(30) Foreign Application Priority Data

Jan. 29, 2013 (EP) .................................. 13153094
Feb. 27, 2013 (GB) .................................. 1303494.7

(51) Int. Cl.

| C07D 273/01 | (2006.01) |
|---|---|
| C07D 405/12 | (2006.01) |
| A61K 31/35 | (2006.01) |
| A61K 31/435 | (2006.01) |
| A61K 31/4355 | (2006.01) |
| A61K 45/06 | (2006.01) |
| A61K 31/33 | (2006.01) |

(52) U.S. Cl.
CPC ............ *C07D 405/12* (2013.01); *A61K 31/33* (2013.01); *A61K 31/435* (2013.01); *A61K 31/4355* (2013.01); *A61K 45/06* (2013.01); *C07D 273/01* (2013.01)

(58) Field of Classification Search
CPC .... C07D 273/01; C07D 405/12; A61K 31/35; A61K 31/435; A61K 31/4355; A61K 45/06
See application file for complete search history.

(56) References Cited

U.S. PATENT DOCUMENTS

| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |

FOREIGN PATENT DOCUMENTS

| WO | 2011107608 A1 | 9/2011 |
| WO | 2013030216 A1 | 3/2013 |
| WO | 2013030365 A1 | 3/2013 |
| WO | 2013030366 A1 | 3/2013 |
| WO | 2013030367 A1 | 3/2013 |

OTHER PUBLICATIONS

Iwakubo, et al., Design and synthesis of rho kinase inhibitors (II), Bioorganic &, Medicinial Chemistry 15 (2007), pp. 350-364.
Iwakubo, et al., Design and synthesis of rho kinase inhibitors (III), Bioorganic &, Medicinial Chemistry 15 (2007), pp. 1022-1033.
Schroeter, et al., Detection of myosin light chain phosphorylation—A cell-based assay for screening Rho-kinase inhibitors, Biochemical and Biophysical Research Communication 374 (2008), pp. 356-360.
International Search Report pertaining to PCT/EP2014/051546 filed Jan. 27, 2014.
Written Opinion pertaining to PCT/EP2014/051546 filed Jan. 27, 2014.

*Primary Examiner* — Timothy R Rozof
(74) *Attorney, Agent, or Firm* — Dinsmore & Shohl LLP

(57) ABSTRACT

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including Respiratory and Gastro-Intestinal diseases.

7 Claims, 1 Drawing Sheet

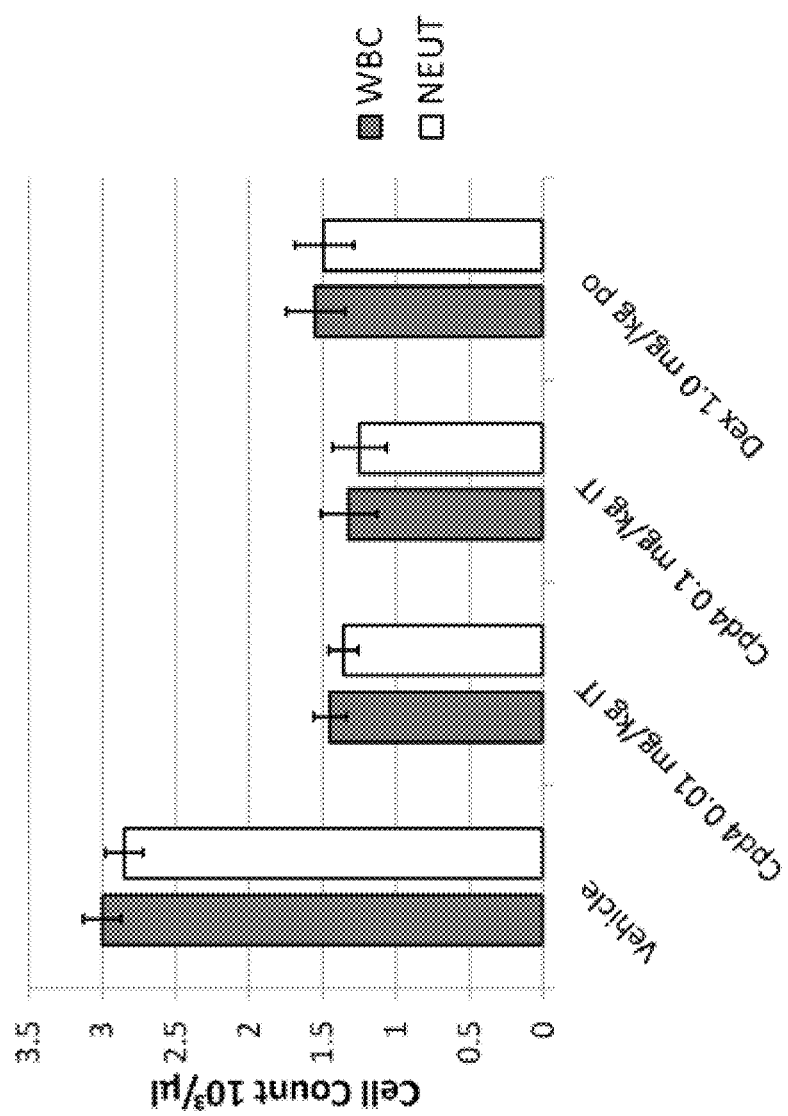

US 9,850,234 B2

PYRIDINE DERIVATIVES AS SOFT ROCK INHIBITORS

CROSS-REFERENCE TO RELATED APPLICATIONS

This application is filed under 35 U.S.C. §111 as a continuation of U.S. application Ser. No. 14/763,594, filed on Jul. 27, 2015, which is a U.S. National Stage Entry under 35 U.S.C. §371 of International Patent Application No. PCT/EP2014/051546, filed on Jan. 27, 2014, which designates the United States and claims priority to United Kingdom Application No. 1303494.7, filed on Feb. 27, 2013, and also claims priority to European Patent Office Application No. 13153094.1, filed on Jan. 29, 2013, the contents of which are hereby incorporated by reference in their entirety.

FIELD OF THE INVENTION

The present invention relates to new kinase inhibitors, more specifically Rho-associated protein kinase (ROCK) inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease.

BACKGROUND OF THE INVENTION

The serine/threonine protein kinase ROCK consists in humans of two isoforms ROCK I and ROCK II. ROCK I is encoded on chromosome 18 whereas ROCK II, also called Rho-kinase, is located on chromosome 12. They both have a molecular weight close to 160 kDa. They share an overall homology of 65% while being 95% homologous in their kinase domains. Despite their sequence similarity, they differ by their tissue distributions. The highest levels of expression for ROCK I are observed in heart, lung and skeletal tissues whereas ROCK II is mostly expressed in brain. Recent data indicate that these two isoforms are partially function redundant, ROCK I being more involved in immunological events, ROCK II in smooth muscle function. The term ROCK refers to ROCK I (ROK-β, p160ROCK, or Rho-kinase β) and ROCK II (ROCK-α or Rho-kinase α).

ROCK activity has been shown to be enhanced by GTPase RhoA that is a member of the Rho (Ras homologous) GTP-binding proteins. The active GTP-bound state of RhoA interacts with Rho-binding domain (RBD) of ROCK that is located in an autoinhibitory carboxyl-terminal loop. Upon binding, the interactions between the ROCK negative regulatory domain and the kinase domain are disrupted. The process enables the kinase to acquire an open conformation in which it is fully active. The open conformation is also induced by the binding of lipid activators such as arachidonic acid to the PH domain in the kinase carboxyl-terminal domain. Another activation mechanism has been described during apoptosis and involves the cleavage of carboxyl terminus by caspase-3 and -2 (or granzyme B) for ROCK I and II, respectively.

ROCK plays an important role in various cellular functions such as smooth muscle contraction, actin cytoskeleton organization, platelet activation, downregulation of myosin phosphatase cell adhesion, -migration, -proliferation and survival, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, wound healing, cell transformation and gene expression. ROCK also acts in several signaling pathways that are involved in auto-immunity and inflammation. ROCK has been shown to play a part in the activation of NF-κB, a critical molecule that leads to the production of TNF and other inflammatory cytokines. ROCK inhibitors are reported to act against TNF-alpha and IL-6 production in lipopolysaccharide (LPS)-stimulated THP-1 macrophages. Therefore, ROCK inhibitors provide a useful therapy to treat autoimmune and inflammatory diseases as well as oxidative stress.

In conclusion, ROCK is a major control point in smooth muscle cell function and a key signaling component involved in inflammatory processes in various inflammatory cells as well as fibrosis and remodeling in many diseased organs. There are clear indications that ROCK is involved in the pathogenesis of many diseases, including asthma, COPD and glaucoma. In addition, ROCK has been implicated in various diseases and disorders including eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythmatosis, spasm, hypertension, chronic obstructive bladder disease, premature birth, infection, allergy, obesity, pancreatic disease and AIDS.

ROCK appears to be a safe target, as exemplified by knockout models and a large number of academic studies. These KO mice data, in combination with post-marketing surveillance studies with Fasudil, a moderately potent ROCK inhibitor used for the treatment of vasospasm after subarachnoid hemorrhage, indicate that ROCK is a genuine and significant drug target.

ROCK inhibitors would be useful as therapeutic agents for the treatment of disorders implicated in the ROCK pathway. Accordingly, there is a great need to develop ROCK inhibitors that are useful in treating various diseases or conditions associated with ROCK activation, particularly given the inadequate treatments currently available for the majority of these disorders. Some non-limiting examples are inflammatory bowel disease, ulcerative colitis, Crohn's disease, asthma, COPD, pulmonary hypertension and idiopathic pulmonary fibrosis.

Allergic asthma is a chronic inflammatory airway disorder that results from maladaptive immune responses to ubiquitous environmental proteins in genetically susceptible persons. Despite reasonably successful therapies, the prevalence increases as these therapies do not cure; there are still exacerbations and an increasing number of non-responders. New, effective and steroid-sparing treatments that tackle all components of the disease are required.

Chronic Obstructive Pulmonary Disease (COPD) represents a group of diseases characterized by irreversible limitation of airflow, associated with abnormal inflammatory response, bronchoconstriction and remodeling and destruction of the tissue of the lung. It is one of the leading causes of death worldwide, with a steadily increasing prevalence. There is an urgent need for novel therapeutic approaches as the current regimen is inadequate. Until recently, only bronchodilators were used, since glucocorticoids have limited or no effect. Roflumilast (Daxas, Dallresp) was approved in 2010 for the treatment of COPD, but is associated with several dose-limiting side effects. Reference ROCK inhibitors, such as Y-27632 relax human isolated bronchial preparations, inhibit increases in airway resistance in anaesthetised animals, potentiate relaxing effects of β-agonists in vitro and in vivo and give rapid bronchodilatation upon inhalation. In addition, ROCK inhibitors block tracheal smooth muscle contractions induced by $H_2O_2$, the clinical marker for oxidative stress.

Related to airway inflammation, ROCK inhibitors counteract the increase in trans-endothelial permeability mediated by inflammatory agents, maintain the endothelial barrier integrity, inhibit the influx of eosinophils after ovalbumin challenge in vivo, protect against lung edema formation and neutrophile migration, suppress airway HR to metacholine and serotonin in allergic mice and block LPS-induced TNF release. With respect to airway fibrosis and remodeling, ROCK inhibitors block the induced migration of airway smooth muscle cells. In vitro evidences for the role of ROCK in airway remodeling were obtained in human lung carcinoma cell line, bovine tracheal smooth muscle cells and human airway smooth muscle. In vivo proof for a role of ROCK in fibrosis in general was generated with mice which exhibited attenuated myocardial fibrosis in response to the partial deletion of ROCK. The attenuation of myocardial fibrosis by Y-27632 in response to myocardial infarction and by fasudil in the case of congestive heart failure in a chronic hypertensive rat model brings additional indications of ROCK's importance in remodeling. Finally, ROCK inhibitors increase apoptotic cell loss of smooth muscle cells.

Several different classes of ROCK inhibitors are known. The current focus is oncology and cardiovascular applications. Until now, the outstanding therapeutic potential of ROCK inhibitors has only been explored to a limited extent. The reason is the fact that ROCK is such a potent and widespread biochemical regulator, that systemic inhibition of ROCK leads to strong biological effects that are considered as being side effects for the treatment of most diseases. Indeed, the medical use of ROCK inhibitors to treat diseases with a strong inflammatory component is hampered by the pivotal role of ROCK in the regulation of the tonic phase of smooth muscle cell contraction. Systemically available ROCK inhibitors induce a marked decrease in blood pressure. Therefore, ROCK inhibitors with different properties are highly required.

For the target specific treatment of disorders by regulating smooth muscle function and/or inflammatory processes and/or remodeling, it is highly desired to deliver a ROCK inhibitor to the target organ and to avoid significant amounts of these drugs to enter other organs. Therefore, local or topical application is desired. Typically, topical administration of drugs has been applied for the treatment of airway-, eye, sexual dysfunction and skin disorders. In addition, local injection/infiltration into diseased tissues further extend the potential medical use of locally applied ROCK inhibitors. Given certain criteria are fulfilled; these local applications allow high drug concentration to be reached in the target tissue. In addition, the incorporation of ROCK inhibitors into implants and stents can further expand the medical application towards the local treatment of CV diseases such as atherosclerosis, coronary diseases and heart failure.

Despite the fact that direct local application is preferred in medical practice, there are concerns regarding drug levels reached into the systemic circulation. For example the treatment of airway diseases by local delivery by for instance inhalation, poses the risk of systemic exposure due to large amounts entering the GI tract and/or systemic absorption through the lungs. Also for dermal applications, local injections and implantable medical devices, there is a severe risk of leakage into the systemic circulation. Therefore, in addition to physical local application, the compounds should preferably have additional chemical or biological properties that will minimize systemic exposure.

Soft drugs are pharmacologically active compounds that are inactivated once they enter the systemic circulation. This inactivation can be achieved in the liver, but the preferred inactivation should occur in the blood. These compounds, once applied locally to the target tissue/organ exert their desired effect locally. When they leak out of this tissue into the systemic circulation, they are very rapidly inactivated. Thus, soft drugs of choice are sufficiently stable in the target tissue/organ to exert the desired biological effect, but are rapidly degraded in the blood to pharmacologically inactive compounds.

In conclusion, there is a continuing need to design and develop soft ROCK inhibitors for the treatment of a wide range of disease states. The compounds described herein and pharmaceutically acceptable compositions thereof are useful for treating or lessening the severity of a variety of disorders or conditions associated with ROCK activation. More specifically, the compounds of the invention are preferably used in the prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration and remodeling. For example, the compounds of the invention may be used in the prevention and/or treatment of diseases and disorders such as:

Airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, Throat, Nose and Ear diseases: including but not limited to sinus problems, hearing problems, toothache, tonsillitis, ulcer and rhinitis, Skin diseases: including but not limited to hyperkeratosis, parakeratosis, hypergranulosis, acanthosis, dyskeratosis, spongiosis and ulceration.

Intestinal diseases: including but not limited to inflammatory bowel disease (IBD), colitis, gastroenteritis, ileus, ileitis, appendicitis and Crohn's disease.

Cardiovascular and vascular diseases: including but not limited to, pulmonary hypertension and pulmonary vasoconstriction.

Inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis.

Neurological disorders: including but not limited to neuropathic pain. The present compounds are therefore suitable for preventing neurodegeneration and stimulating neurogeneration in various neurological disorders.

Proliferative diseases: such as but not limited to cancer of, breast, colon, intestine, skin, head and neck, nerve, lung, pancreas, or thyroid gland; Castleman disease; malignoma; and melanoma.

Bone diseases: including but not limited to osteoporosis and osteoarthritis

In addition, the compounds of the invention may be used in the prevention and/or treatment of diseases and disorders such as benign prostatic hyperplasia, transplant rejection, spasm, chronic obstructive bladder disease, and allergy.

SUMMARY OF THE INVENTION

We have surprisingly found that the compounds described herein act as inhibitors of ROCK, in particular as soft ROCK inhibitors. As can be seen from the examples, the compounds of the present invention are very rapidly converted into pharmacologically inactive compounds for example by carboxylic ester hydrolases (EC 3.1.1) such as Paraoxonase 1 (PON1) or by plasma proteins displaying pseudoesterase activity such as Human serum albumin. Carboxylic ester hydrolases (EC 3.1.1) represent a large group of enzymes involved in the degradation of carboxylic esters into alcohols and carboxylic acids. As such, enzymes displaying this catalytic activity are of potential interest for the design of soft kinase inhibitors. EC 3.1.1 includes the following sub-classes:

EC 3.1.1.1 carboxylesterase; EC 3.1.1.2 arylesterase; EC 3.1.1.3 triacylglycerol lipase; EC 3.1.1.4 phospholipase A2; EC 3.1.1.5 lysophospholipase; EC 3.1.1.6 acetylesterase; EC 3.1.1.7 acetylcholinesterase; EC 3.1.1.8 cholinesterase; EC 3.1.1.10 tropinesterase; EC 3.1.1.11 pectinesterase; EC 3.1.1.13 sterol esterase; EC 3.1.1.14 chlorophyllase; EC 3.1.1.15 L-arabinonolactonase; EC 3.1.1.17 gluconolactonase; EC 3.1.1.19 uronolactonase; EC 3.1.1.20 tannase; EC 3.1.1.21 retinyl-palmitate esterase; EC 3.1.1.22 hydroxybutyrate-dimer hydrolase; EC 3.1.1.23 acylglycerol lipase; EC 3.1.1.24 3-oxoadipate enol-lactonase; EC 3.1.1.25 1,4-lactonase; EC 3.1.1.26 galactolipase; EC 3.1.1.27 4-pyridoxolactonase; EC 3.1.1.28 acylcarnitine hydrolase; EC 3.1.1.29 aminoacyl-tRNA hydrolase; EC 3.1.1.30 D-arabinonolactonase; EC 3.1.1.31 6-phosphogluconolactonase; EC 3.1.1.32 phospholipase A1; EC 3.1.1.33 6-acetylglucose deacetylase; EC 3.1.1.34 lipoprotein lipase; EC 3.1.1.35 dihydrocoumarin hydrolase; EC 3.1.1.36 limonin-D-ring-lactonase; EC 3.1.1.37 steroid-lactonase; EC 3.1.1.38 triacetate-lactonase; EC 3.1.1.39 actinomycin lactonase; EC 3.1.1.40 orsellinate-depside hydrolase; EC 3.1.1.41 cephalosporin-C deacetylase; EC 3.1.1.42 chlorogenate hydrolase; EC 3.1.1.43 α-amino-acid esterase; EC 3.1.1.44 4-methyloxaloacetate esterase; EC 3.1.1.45 carboxymethylenebutenolidase; EC 3.1.1.46 deoxylimonate A-ring-lactonase; EC 3.1.1.47 1-alkyl-2-acetylglycerophosphocholine esterase; EC 3.1.1.48 fusarinine-C ornithinesterase; EC 3.1.1.49 sinapine esterase; EC 3.1.1.50 wax-ester hydrolase; EC 3.1.1.51 phorbol-diester hydrolase; EC 3.1.1.52 phosphatidylinositol deacylase; EC 3.1.1.53 sialate 0-acetylesterase; EC 3.1.1.54 acetoxybutynylbithiophene deacetylase; EC 3.1.1.55 acetylsalicylate deacetylase; EC 3.1.1.56 methylumbelliferyl-acetate deacetylase; EC 3.1.1.57 2-pyrone-4,6-dicarboxylate lactonase; EC 3.1.1.58 N-acetylgalactosaminoglycan deacetylase; EC 3.1.1.59 juvenile-hormone esterase; EC 3.1.1.60 bis(2-ethylhexyl)phthalate esterase; EC 3.1.1.61 protein-glutamate methylesterase; EC 3.1.1.63 11-cis-retinyl-palmitate hydrolase; EC 3.1.1.64 all-trans-retinyl-palmitate hydrolase; EC 3.1.1.65 L-rhamnono-1,4-lactonase; EC 3.1.1.66 5-(3,4-diacetoxybut-1-ynyl)-2,2'-bithiophene deacetylase; EC 3.1.1.67 fatty-acyl-ethyl-ester synthase; EC 3.1.1.68 xylono-1,4-lactonase; EC 3.1.1.70 cetraxate benzylesterase; EC 3.1.1.71 acetylalkylglycerol acetylhydrolase; EC 3.1.1.72 acetylxylan esterase; EC 3.1.1.73 feruloyl esterase; EC 3.1.1.74 cutinase; EC 3.1.1.75 poly(3-hydroxybutyrate) depolymerase; EC 3.1.1.76 poly(3-hydroxyoctanoate) depolymerase; EC 3.1.1.77 acyloxyacyl hydrolase; EC 3.1.1.78 polyneuridine-aldehyde esterase; EC 3.1.1.79 hormone-sensitive lipase; EC 3.1.1.80 acetylajmaline esterase; EC 3.1.1.81 quorum-quenching N-acyl-homoserine lactonase; EC 3.1.1.82 pheophorbidase; EC 3.1.1.83 monoterpene ϵ-lactone hydrolase; EC 3.1.1.84 cocaine esterase; EC 3.1.1.85 mannosylglycerate hydrolase;

An example of carboxylic ester hydrolase of particular relevance with respect to the compounds of the present invention is PON1. PON1 is a $Ca^{2+}$ dependent serum class A-esterase, which is synthesized in the liver and secreted in the blood, where it associates exclusively with high-density lipoproteins (HDLs). Furthermore, it is able to cleave a unique subset of substrate including organophosphates, arylesters, lactones and cyclic carbonates. Therefore, the Y substituent of the compounds of the present invention, generally represented by formula I hereinbelow, are selected to comprise a substituent selected from a group of lactones.

The compounds of the present invention differ from those disclosed in application WO2011107608 from the same applicant at least in the presence of the Cy group. Furthermore, the compounds of the invention display an unexpected and more favorable combination of strong on-target potency and fast degradation in human plasma in comparison to those compounds.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, salt, hydrate, or solvate thereof,

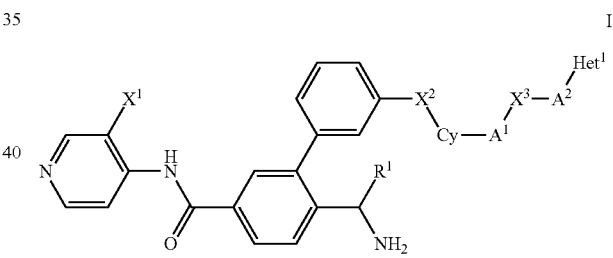

Wherein $R^1$ is selected from hydrogen and $C_{1-20}$alkyl;

$X^1$ is hydrogen or halo;

$X^2$ is —C(=O)—NH— or —NH—C(=O)—;

Cy is an optionally substituted group selected from aryl and heteroaryl;

$X^3$ is selected from the group consisting of —S—, —O—, and —$NR^2$—;

$R^2$ is hydrogen or $C_{1-6}$alkyl;

$Het^1$ is 2-oxotetrahydrofuranyl optionally substituted with one or more $C_{1-6}$alkyl-; and $A^1$ and $A^2$ are each independently a direct bond or an optionally substituted $C_{1-6}$alkylene.

Viewed from a further aspect, the invention provides the use of a compound of the invention, or a composition comprising such a compound, for inhibiting the activity of at least one kinase, in vitro or in vivo.

Viewed from a further aspect, the invention provides the use of a compound of the invention, or a composition comprising such a compound, for inhibiting the activity of at least one ROCK kinase, for example ROCKII and/or ROCKI isoforms.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of at least one disease and/or disorder selected from the group comprising airway diseases; throat, nose and ear diseases; intestinal diseases; cardiovascular and vascular diseases; inflammatory diseases; skin diseases, neurological disorders; proliferative diseases; bone diseases; transplant rejection, spasm, chronic obstructive bladder disease, allergy.

BRIEF DESCRIPTION OF THE DRAWINGS

With specific reference now to the FIGURES, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 1: Anti-inflammatory activity of Cpd4 in an acute LPS lung challenge model (mouse). Data is provided as bronchoalveolar lavage fluid (BALF) cell count ($10^3/\mu l$) ±SEM. WBC: White Blood Cell. NEUT: Neutrophil. Dex: Dexamethasone control.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I

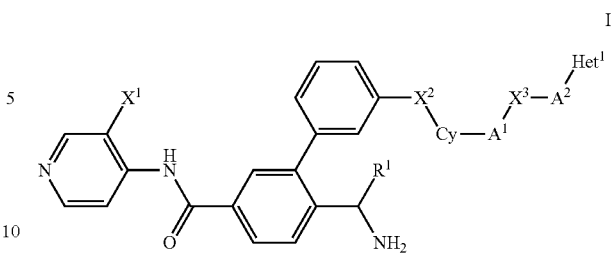

wherein $X^1$, $X^2$, $X^3$, Cy, $R^1$, $Het^1$, $A^1$ and $A^2$ are as defined hereinbefore, including the stereo-isomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, isobutynyl, pentynyl, hexynyl, and the like. An optionally substituted alkynyl refers to an alkynyl having optionally one or more substituents, selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure(s). Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2CH_2$-*, *—$CH$(—$CH_2CH_3$)—*, or *—$CH_2CH$(—$CH_3$)—*. Likewise a $C_3$ cycloalkylene group may be

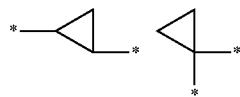

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocyclyl" or "heterocycle" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-h]furanyl, thieno[3,2-h]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is C$_1$-C$_{10}$ alkoxy, C$_1$-C$_6$ alkoxy, or C$_1$-C$_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —R$^d$—R$^c$ wherein R$^d$ is alkylene or alkylene substituted by alkyl group and R$^c$ is a heterocyclyl group.

The term "carboxy" or "carboxyl" or "hydroxycarbonyl" by itself or as part of another substituent refers to the group —CO$_2$H. Thus, a carboxyalkyl is an alkyl group as defined above having at least one substituent that is —CO$_2$H.

The term "alkoxycarbonyl" by itself or as part of another substituent refers to a carboxy group linked to an alkyl radical i.e. to form —C(=O)OR$^e$, wherein R$^e$ is as defined above for alkyl.

The term "alkylcarbonyloxy" by itself or as part of another substituent refers to a —O—C(=O)R$^e$ wherein R$^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —OCF$_3$, —OCHF$_2$, —OCH$_2$F, —O—CF$_2$—CF$_3$, —O—CH$_2$—CF$_3$, —O—CH$_2$—CHF$_2$, and —O—CH$_2$—CH$_2$F.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted with once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted as examples, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a second embodiment, the present invention provides those compounds of formula I wherein;

$R^1$ is selected from hydrogen and $C_{1-6}$alkyl; in particular $R^1$ is hydrogen.

In another embodiment, the present invention provides compounds of formula I as described herein, wherein $X^1$ is halo; in particular fluoro.

In yet another embodiment, the present invention provides those compounds of formula I, wherein $X^2$ is —C(=O)—NH—.

In a particular embodiment, the present invention provides compounds of formula I, wherein Cy is an optionally substituted aryl.

In a further embodiment, the present invention provides compounds of formula I as described herein, wherein the optional substituents in the Cy definition are one or more substituents selected from halo, hydroxyl, oxo, carbonyl, amino, amido, cyano, aryl, heteroaryl, $C_{3-8}$cycloalkyl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$alkoxy, halo-$C_{1-8}$alkyl, thiol, $C_{1-8}$alkylthio, carboxylic acid, acylamino, $C_{1-8}$alkyl ester, carbamate, thioamido, urea, and sulfonamide.

In another further embodiment, the present invention provides compounds of formula I as described herein, wherein the optional substituents in the Cy definition are one or more substituents selected from $C_{1-6}$ alkyl, $C_{1-6}$ alkoxyl, $C_{1-6}$ haloalkyl, $C_{1-6}$ haloalkoxyl, and halo, in particular $C_{1-6}$alkyl or halo; more in particular halo.

In another embodiment, the present invention provides compounds of formula I as described herein, wherein Cy is optionally substituted with one substituent as described herein.

In a particular embodiment, the present invention provides compounds of formula I as described herein, wherein Cy is a six-membered ring.

In a further embodiment, -$A^1$-$X^3$-$A^2$-$Het^1$ is substituted on Cy in the meta or para position of $X^2$; in particular in the para position.

In a particular embodiment, the present invention provides compounds of formula I, wherein $R^2$ is hydrogen or $C_{1-3}$alkyl; in particular hydrogen or methyl.

In particular embodiment, the present invention provides compounds of formula I, wherein $Het^1$ is selected from

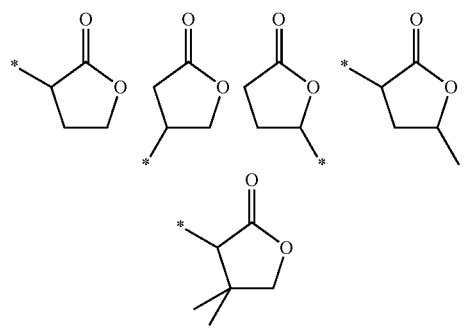

In another particular embodiment, the present invention provides compounds of formula I, wherein $Het^1$ is selected from

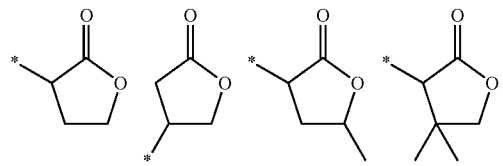

In a particular embodiment, $A^1$ and $A^2$ are independently a direct bond or a $C_{1-6}$alkylene, wherein said $C_{1-6}$alkylene is optionally substituted with one or more substituents selected from the group consisting of $C_{1-6}$alkyl, $C_{1-6}$alkenyl, $C_{1-6}$alkynyl, halo, hydroxyl, oxo, amino, cyano, aryl, heteroaryl, cycloalkyl, alkylamino, alkoxy, alkylthio, acylamino, carbamate, urea, and sulfonamido; in particular from the group consisting of halo, hydroxyl, oxo, amino, amido, cyano, aryl, heteroaryl, $C_{3-8}$cycloalkyl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$alkoxy, halo-$C_{1-8}$alkyl, $C_{1-8}$alkylthio, acylamino, carbamate, urea, and sulfonamide.

In a more particular embodiment, $A^1$ and $A^2$ are independently a direct bond or a $C_{1-6}$alkylene, wherein said $C_{1-6}$alkylene is optionally substituted with one substituent; more in particular with one substituent selected from the group consisting of $C_{1-6}$alkyl, $C_{1-6}$alkenyl, $C_{1-6}$alkynyl, halo, hydroxyl, oxo, amino, cyano, aryl, heteroaryl, cycloalkyl, alkylamino, alkoxy, alkylthio, acylamino, carbamate, urea, and sulfonamido; in particular from the group consisting of halo, hydroxyl, oxo, amino, amido, cyano, aryl, heteroaryl, $C_{3-8}$cycloalkyl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$ alkoxy, halo-$C_{1-8}$alkyl, $C_{1-8}$alkylthio, acylamino, carbamate, urea, and sulfonamide.

In another embodiment, $A^1$ and $A^2$ are each independently a direct bond or a $C_{1-6}$alkylene, wherein said $C_{1-6}$alkylene is optionally substituted with one or more $C_{1-6}$alkyl groups.

In a further embodiment, $A^1$ and $A^2$ are each independently a direct bond or an optionally substituted $C_{1-4}$alkylene, in particular a direct bond or an optionally substituted $C_{1-2}$alkylene. In one embodiment $A^1$ and $A^2$ are each independently a direct bond or an unsubstituted $C_{1-4}$alkylene.

In a further embodiment, $A^1$ is a direct bond. In another further embodiment, $A^2$ is a direct bond. In another embodiment $A^1$ and $A^2$ are a direct bond.

In another particular embodiment, $A^1$ is —$(CH_2)$—$_m$, wherein m is an integer from 0 to 4.

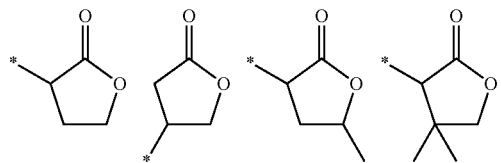

In yet another particular embodiment, $A^2$ is —$(CH_2)_n$—, wherein n is an integer from 0 to 4.

In yet another particular embodiment, n and m are each independently 0, 1 or 2.

It is also an object of the present invention to provide those compounds of formula I wherein one or more of the following restriction apply:

$R^1$ is selected from hydrogen and $C_{1-6}$alkyl; in particular hydrogen;

$X^1$ is halo; in particular fluoro;

$X^2$ is —C(=O)—NH—;

$X^2$ is —NH—C(=O)—;

Cy is an optionally substituted aryl;

the optional substituents in the Cy definition are one or more substituents selected from aryl, heteroaryl, and $C_{3-10}$cycloalkyl; wherein said aryl, heteroaryl and $C_{3-10}$cycloalkyl is optionally substituted with one or more substituents selected from the group consisting of halo, hydroxyl, oxo, carbonyl, amino, amido, cyano, aryl, heteroaryl, $C_{3-8}$cycloalkyl, $C_{3-8}$heterocyclyl, $C_{1-8}$alkylamino, $C_{1-6}$alkyl, di($C_{1-8}$alkyl)amino, $C_{1-8}$alkoxy, halo-$C_{1-8}$alkoxy, halo-$C_{1-8}$alkyl, thiol, $C_{1-8}$alkylthio, carboxylic acid, acylamino, $C_{1-8}$alkyl ester, carbamate, thioamido, urea, and sulfonamide;

the optional substituents in the Cy definition are one or more substituents selected from $C_{1-6}$ alkyl, $C_{1-6}$ alkoxyl, $C_{1-6}$ haloalkyl, $C_{1-6}$ haloalkoxyl, and halo; in particular halo;

Cy is optionally substituted with one substituent;

Cy is a six-membered ring;

$A^1$-$X^3$$A^2$-$Het^1$ is substituted on Cy in the meta or para position of $X^2$; in particular in the para position $R^2$ is hydrogen or $C_{1-3}$alkyl; in particular hydrogen or methyl;

$Het^1$ is selected from the group comprising

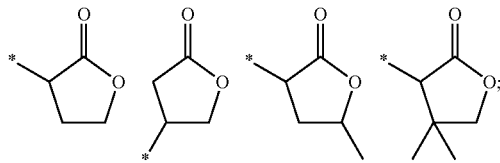

$A^1$ and $A^2$ are independently a direct bond or a $C_{1-6}$alkylene, wherein said $C_{1-6}$alkylene is optionally substituted with one or more substituents selected from the group consisting of $C_{1-6}$alkyl, $C_{1-6}$alkenyl, $C_{1-6}$alkynyl, halo, hydroxyl, oxo, amino, cyano, aryl, heteroaryl, cycloalkyl, alkylamino, alkoxy, alkylthio, acylamino, carbamate, urea, and sulfonamido;

$A^1$ and $A^2$ are independently a direct bond or a $C_{1-6}$alkylene, wherein said $C_{1-6}$alkylene is optionally substituted with one or more substituents selected from the group consisting of halo, hydroxyl, oxo, amino, amido, cyano, aryl, heteroaryl, $C_{3-8}$cycloalkyl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$alkoxy, halo-$C_{1-8}$alkyl, $C_{1-8}$alkylthio, acylamino, carbamate, urea, and sulfonamide;

$A^1$ and $A^2$ are each independently a direct bond or a $C_{1-6}$alkylene, wherein said $C_{1-6}$alkylene is optionally substituted with one or more $C_{1-6}$alkyl groups;

$A^1$ is —$(CH_2)$—$_m$, wherein m is an integer from 0 to 4;

$A^2$ is —$(CH_2)$—$_n$, wherein n is an integer from 0 to 4

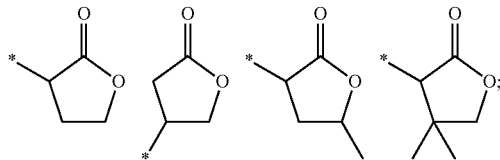

and n and m are each independently 0, 1 or 2; in particular 0 or 1.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as kinase inhibitors, more in particular for the inhibition of at least one ROCK kinase, selected from ROCKI and ROCKII, in particular soft ROCK inhibitors.

The present invention further provides the use of a compound as defined hereinbefore or the use of a composition comprising said compound, as a human or veterinary medicine, in particular for prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeration, function, inflammation, fibrosis, excessive cell proliferation, excessive angiogenesis, hyperreactivity, barrier dysfunction, neurodegeration and remodeling.

In a further embodiment, the invention provides the use of a compound as defined hereinbefore, or the use of a composition comprising said compound in the prevention and/or treatment of at least one disease or disorder selected from the group comprising airway diseases; throat, nose and ear diseases; intestinal diseases; cardiovascular and vascular diseases; inflammatory diseases; skin diseases; neurological and CNS disorders; proliferative diseases; bone diseases; transplant rejection, spasm, chronic obstructive bladder disease, allergy.

In a preferred embodiment, the invention provides the use of a compound as defined hereinbefore or the use of a composition comprising said compound in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith.

In a further embodiment, the invention provides the use of a compound as defined hereinbefore or the use of a composition comprising said compound in the prevention and/or treatment of cardiovascular and vascular diseases: including but not limited to pulmonary hypertension and pulmonary vasoconstriction, and/or for preventing, treating and/or alleviating complications and/or symptoms associated therewith and/or alleviating complications and/or symptoms associated therewith.

In a further embodiment, the invention provides the use of a compound as defined hereinbefore or the use of a composition comprising said compound in the prevention and/or treatment of Throat, Nose and Ear diseases: including but not limited to sinus problems, hearing problems, toothache, tonsillitis, ulcer and rhinitis, In a further embodiment, the invention provides the use of a compound as defined hereinbefore or the use of a composition comprising said compound in the prevention and/or treatment of skin diseases: including but not limited to hyperkeratosis, parakeratosis, hypergranulosis, acanthosis, dyskeratosis, spongiosis and ulceration.

In a further embodiment, the invention provides the use of a compound as defined hereinbefore or the use of a composition comprising said compound in the prevention and/or treatment of Intestinal diseases; including but not limited to inflammatory bowel disease (IBD), colitis, gastroenteritis, ileus, ileitis, appendicitis and Crohn's disease.

In yet another embodiment, the invention provides the use of a compound as defined hereinbefore or the use of a composition comprising said compound in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides the use of a compound as defined hereinbefore or the use of a composition comprising said compound in the prevention, treatment and/or management of neurological disorders: including but not limited to neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides the use of a compound as defined hereinbefore or the use of a composition comprising said compound in the prevention and/or treatment of proliferative diseases: such as but not limited to cancer of the breast, colon, intestine, skin, head and neck, nerve, lung, liver, pancreas, or thyroid gland; Castleman disease malignoma; and melanoma; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diseases and disorders such as benign prostatic hyperplasia, transplant rejection, spasm, chronic obstructive bladder disease, allergy, and/or for preventing, treating and/or alleviating complications and/or symptoms associated therewith.

In a preferred embodiment the present invention provides the use of a compound as defined hereinbefore or the use of a composition comprising said compound in the prevention and/or treatment of asthma or COPD.

Method of Treatment

The present invention further provides a method for the prevention and/or treatment of at least one disease or disorder selected from the group comprising airway diseases; cardiovascular diseases, inflammatory diseases; skin diseases, neurological disorders; proliferative diseases; bone diseases; transplant rejection; spasm; chronic obstructive bladder disease and allergy; said method comprising administering to a subject in need thereof a therapeutic effective amount of a compound or a composition as defined herein.

In a preferred embodiment, the invention provides a method for the prevention and/or treatment of airway diseases including but not limited to pulmonary fibrosis, emphysema, chronic bronchitis, asthma, fibrosis, pneumonia, cystic fibrosis, chronic obstructive pulmonary disease (COPD) bronchitis, rhinitis, and respiratory distress syndrome; said method comprising administering to a subject in need thereof a therapeutic effective amount of a compound or a composition as defined herein.

In another embodiment, the invention provides a method for the prevention and/or treatment of cardiovascular and vascular diseases: including but not limited to pulmonary hypertension and pulmonary vasoconstriction; said method comprising administering to a subject in need thereof a therapeutic effective amount of a compound or a composition as defined herein.

In another embodiment, the invention provides a method for the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis; said method comprising administering to a subject in need thereof a therapeutic effective amount of a compound or a composition as defined herein.

In another embodiment, the invention provides a method for the prevention and/or treatment of neurological disorders: including but not limited to neuropathic pain. The present compounds are therefore suitable for preventing neurodegeneration and stimulating neurogeneration in various neurological disorders; said method comprising administering to a subject in need thereof a therapeutic effective amount of a compound or a composition as defined herein.

In another embodiment, the invention provides a method for the prevention and/or treatment of proliferative diseases: such as but not limited to cancer of the breast, colon, intestine, skin, head and neck, nerve, lung, liver, pancreas, or thyroid gland; Castleman disease; sarcoma; malignoma; and melanoma; said method comprising administering to a subject in need thereof a therapeutic effective amount of a compound or a composition as defined herein.

In another embodiment, the invention provides a method for the prevention and/or treatment of kidney diseases: including but not limited to renal fibrosis or renal dysfunction; said method comprising administering to a subject in need thereof a therapeutic effective amount of a compound or a composition as defined herein.

In another embodiment, the invention provides a method for the prevention and/or treatment of bone diseases: including but not limited to osteoporosis and osteoarthritis; said method comprising administering to a subject in need thereof a therapeutic effective amount of a compound or a composition as defined herein.

In another embodiment, the invention provides a method for the prevention and/or treatment of diseases and disorders such as benign prostatic hyperplasia, transplant rejection, spasm, chronic obstructive bladder disease, and allergy; said method comprising administering to a subject in need thereof a therapeutic effective amount of a compound or a composition as defined herein.

In a preferred embodiment, the invention provides a method for the prevention and/or treatment of airways, intestinal and inflammatory diseases; said method comprising administering to a subject in need thereof a therapeutic effective amount of a compound or a composition as defined herein.

In the invention, particular preference is given to compounds of Formula I or any subgroup thereof that in the inhibition assay for ROCK described below inhibit ROCK with an $IC_{50}$ value of less than 1 µM, preferably less than 0.1 µM.

Said inhibition may be effected in vitro and/or in vivo, and when effected in vivo, is preferably effected in a selective manner, as defined above.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role.

For pharmaceutical use, the compounds of the invention may be used as free base, and/or in the form of a pharmaceutically acceptable acid-addition salt (e.g. obtained with non-toxic organic or inorganic acid), in the form of a hydrate, solvate and/or complex. As used herein and unless otherwise stated, the term "solvate" includes any combination which may be formed by a compound of this invention with a suitable inorganic solvent (e.g. hydrates) or organic solvent.

Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts from inorganic or organic acids. Examples of such acid addition salts include acetate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalene-sulfonate, nicotinate, oxalate, palmoate, pectinate, persulfate, 3-phenylpropionate, picrate, pivalate, propionate, succinate, tartrate, tosylate, and undecanoate. The compounds can be administered by a variety of routes including the oral, rectal, transdermal, or intranasal routes, depending mainly on the specific preparation used and the condition to be treated or prevented. The at least one compound of the invention will generally be administered in an "effective amount", by which is meant any amount of a compound of the Formula I or any subgroup thereof that, upon suitable administration, is sufficient to achieve the desired therapeutic or prophylactic effect in the individual to which it is administered. Such amount will usually vary depending on the condition to be prevented or treated and the route of administration. The amount(s) to be administered, the route of administration and the further treatment regimen may be determined by the treating clinician, depending on factors such as the age, gender and general condition of the patient and the nature and severity of the disease/symptoms to be treated.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Compound Purity

Unless indicated otherwise, the purity of the compounds was confirmed by liquid chromatography/mass spectrometry (LC/MS) and/or proton NMR B. Compound Synthesis B.1. Intermediates Synthetic intermediates were prepared according to the experimental procedures shown below.

Intermediate 1:
3-((4-aminobenzyl)amino)dihydrofuran-2(3H)-one

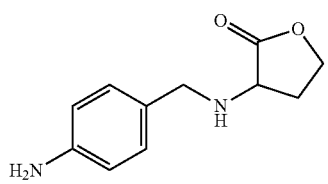 [SMILES: Nc1ccc(CNC2CCOC2=O)cc1]

To a solution of 4-(aminomethyl)aniline (4 g, 32.7 mmol) and 3-bromodihydrofuran-2(3H)-one (3.33 mL, 36.0 mmol) in MeCN (80 mL) was added $K_2CO_3$ (4.07 g, 29.5 mmol). The reaction mixture was stirred at 80° C. overnight. Then the precipitate was filtered off and the filtrate concentrated under vacuum. The residue was purified by flash chromatography (silica gel) eluting with pure EtOAc. The pure fraction was then combined and concentrated under vacuum. The resulting colorless oil was dissolved in DCM and HCl gas was bubbled through to it for 30 s. Finally the precipitate was collected by filtration and washed with $Et_2O$ (×3) to give the HCl salt of the intermediate 1 (2.5 g, 27%) as white powder.

Intermediate 2: 3-(((4-aminophenyl)thio)methyl)dihydrofuran-2(3H)-one

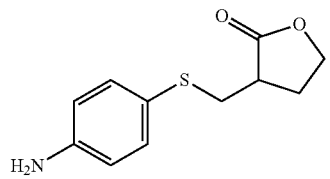

To a solution of 3-methylenedihydrofuran-2(3H)-one (5 g, 50.97 mmol) and $Et_3N$ (10.29 g, 101.9 mmol) in THF (200 mL) was added 4-aminobenzenethiol (12.73 g, 101.9 mmol). The mixture was stirred at room temperature overnight and concentrated. The residue was purified by preparative HPLC to give intermediate 2 (6.5 g, 57%) as brown powder.

Intermediate 3:
3-(4-aminophenoxy)dihydrofuran-2(3H)-one

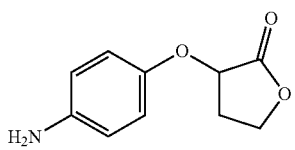

To a solution of 4-aminophenol (4.15 g, 38 mmol) and $Et_3N$ (30 mL, 215 mmol) in methanol (75 mL) was added $Boc_2O$ (9.7 mL, 41.8 mmol) and the reaction mixture was stirred at room temperature overnight. After removal of solvent, the residue was distributed between ethyl acetate (250 mL) and 0.25 N aqueous hydrochloric acid solution (100 mL). The organic phase was isolated, washed with an aqueous saturated ammonium chloride solution (3×50 mL), dried over anhydrous sodium sulfate, filtered and concentrated under vacuum to give the expected compound (4-Hydroxy-phenyl)-carbamic acid tert-butyl ester (6.65 g, 84% yield) as white powder.

To a solution of (4-Hydroxy-phenyl)-carbamic acid tert-butyl ester (2.5 g, 11.95 mmol) and 3-bromodihydrofuran-2(3H)-one (1.66 mL, 17.92 mmol) in MeCN (30 ml) was added $K_2CO_3$ (3.3 g, 23.9 mmol) and the reaction mixture was stirred at 80° C. overnight. After cooling to room temperature, the precipitate was filtered off and the filtrate concentrated under vacuum. The residue was precipitated in $Et_2O$, collected by filtration and dried overnight in the oven (60° C.) to give the expected compound tert-butyl (4-((2-oxotetrahydrofuran-3-yl)oxy)phenyl)carbamate (3.11 g, 89%) as white powder.

To a solution of tert-butyl (4-((2-oxotetrahydrofuran-3-yl)oxy)phenyl)carbamate (3.05 g, 10.38 mmol) in DCM (56 mL) was added TFA (8.0 mL, 104 mmol). The reaction mixture was stirred at room temperature for 2.5 h and concentrated under vacuum. The residue was precipitated in a mixture MeCN/Et$_2$O, collected by filtration and dried in the oven (60° C.) overnight to give the TFA salt of intermediate 3 (2.64 g, 83%) as white powder.

Intermediate 4:
4-((2-oxotetrahydrofuran-3-yl)thio)benzoic acid

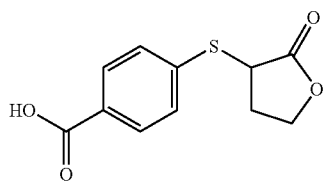 [SMILES: O=C(O)c1ccc(SC2CCOC2=O)cc1]

To a suspension of 4-mercaptobenzoic acid (2 g, 12.97 mmol) in MeCN (30 mL) were added 3-bromodihydrofuran-2(3H)-one (1.318 mL, 14.27 mmol) and Et$_3$N (1.450 mL, 10.4 mmol). The reaction mixture was stirred at 80° C. overnight. The precipitate was filtered off and the filtrate concentrated under vacuum. The residue was suspended in DCM, collected by filtration and washed with DCM and water to give the intermediate 4 (1.79 g, 58%) as white powder.

Similarly, the following intermediate can be obtained by following an analogous experimental protocol.

Intermediate 4a:
4-((2-oxotetrahydrofuran-3-yl)amino)benzoic acid

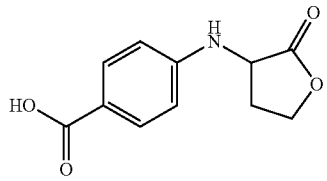 [SMILES: O=C(O)c1ccc(NC2CCOC2=O)cc1]

Intermediate 4a was obtained by using 4-aminobenzoic acid as starting material, instead of 4-mercaptobenzoic acid.

Intermediate 5:
3-((4-aminophenyl)amino)dihydrofuran-2(3H)-one

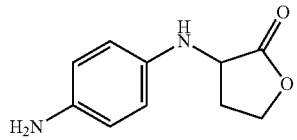

To a solution of tert-butyl (4-aminophenyl)carbamate (3 g, 14.41 mmol) and 3-bromodihydrofuran-2(3H)-one (1.464 mL, 15.85 mmol) in MeCN (30 mL) was added K$_2$CO$_3$ (1.991 g, 14.41 mmol). The reaction mixture was stirred at 80° C. overnight, the precipitate filtered off and the filtrate concentrated under vacuum. The residue was precipitated in Et$_2$O and collected by filtration to give the expected compound tert-butyl (4-((2-oxotetrahydrofuran-3-yl)amino)phenyl)carbamate (3.1 g, 74%) as white powder.

To a solution of tert-butyl (4-((2-oxotetrahydrofuran-3-yl)amino)phenyl)carbamate (1.5 g, 5.13 mmol) in DCM (30 ml) was added TFA (4.29 mL). The reaction mixture was stirred at room temperature overnight and concentrated under vacuum. The residue was diluted in a mixture MeCN/water and freeze-dried to give the TFA salt of the intermediate 5 (1.54 g, 71%) as white powder.

Similarly, the following intermediates can be obtained by following an analogous experimental protocol.

Intermediate 5a: 3-((3-methyl-4-aminophenyl)amino)dihydrofuran-2(3H)-one

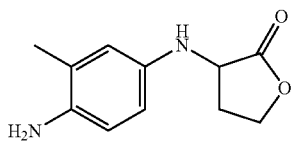

Intermediate 5a was obtained by using tert-butyl (3-methyl-4-aminophenyl)carbamate as starting material, instead of tert-butyl (4-aminophenyl)carbamate.

Intermediate 5b:
3[(2-amino-1,3-thiazol-5-yl)amino]oxolan-2-one

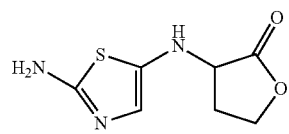 [SMILES: Nc1ncc(NC2CCOC2=O)s1]

Intermediate 5b was obtained by using tert-butyl N-(5-amino-1,3-thiazol-2-yl)carbamate as starting material, instead of tert-butyl (4-aminophenyl)carbamate.

Intermediate 6: 5-oxooxolan-3-yl methanesulfonate

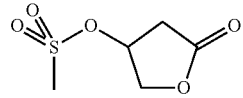

To a solution of 4-hydroxyoxolan-2-one (8 g, 78.4 mmol, 1.0 eq) and dry pyridine (9.3 g, 117.6 mmol, 1.5 eq) in DCM (400 ml) was added MsCl (13.37 g, 117.6 mmol, 1.5 eq) at 0° C. The resulting mixture was stirred overnight at 30° C., and was then washed with 5% aq. HCl, and brine. The organic layer was dried over MgSO$_4$, filtered and the residue was concentrated to provide 5 g of intermediate 6 (35.5% yield).

Intermediate 7: 3-((4-aminophenyl)thio)dihydrofuran-2(3H)-one

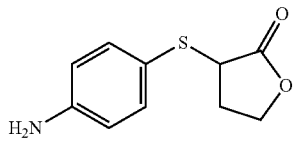 [SMILES: Nc1ccc(SC2CCOC2=O)cc1]

To a suspension of 4-aminobenzenethiol (2 g, 15.98 mmol) in MeCN (30 mL) were added 3-bromodihydrofuran-2(3H)-one (1.623 mL, 17.57 mmol) and triethylamine (2.227 mL, 15.98 mmol). The reaction mixture was stirred at 80° C. for 2 h and concentrated under vacuum. The residue was dissolved in DCM and HCl gas bubbled for 2 min. The precipitate was collected by filtration and washed with DCM and ACN to give the HCl salt of the intermediate 7 (2.7 g, 69%) as white powder.

Similarly, the following intermediates can be obtained by following an analogous experimental protocol.

Intermediate 7a: 3-((3-aminophenyl)thio)dihydrofuran-2(3H)-one

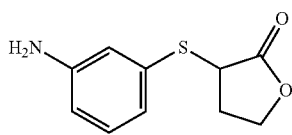 [SMILES: Nc1cccc(SC2CCOC2=O)c1]

Intermediate 7a was obtained by using 3-aminobenzenethiol as starting material, instead of 4-aminobenzenethiol.

Intermediate 7b: 3-((3-fluoro-4-aminophenyl)thio)dihydrofuran-2(3H)-one

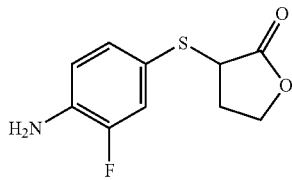 [SMILES: Nc1ccc(SC2CCOC2=O)cc1F]

Intermediate 7b was obtained by using 3-fluoro-4-aminobenzenethiol as starting material, instead of 4-aminobenzenethiol.

Intermediate 7c: 3-((4-aminophenyl)thio)-5-methyldihydrofuran-2(3H)-one

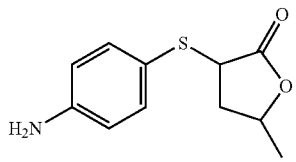

Intermediate 7c was obtained by reacting 4-aminobenzenethiol with 3-bromo-5-methyldihydrofuran-2(3H)-one, instead of 3-bromodihydrofuran-2(3H)-one.

Intermediate 7d: 3-((4-aminophenyl)thio)-4,4-dimethyldihydrofuran-2(3H)-one

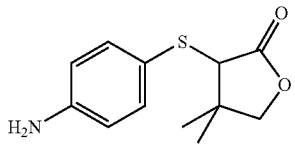

Intermediate 7d was obtained by reacting 4-aminobenzenethiol with 3-bromo-4,4-dimethyldihydrofuran-2(3H)-one, instead of 3-bromodihydrofuran-2(3H)-one.

Intermediate 7e: 4-((4-aminophenyl)thio)dihydrofuran-2(3H)-one

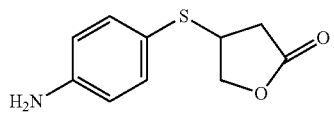

Intermediate 7e was obtained by reacting 4-aminobenzenethiol with 5-oxooxolan-3-yl methanesulfonate (intermediate 6), instead of 3-bromodihydrofuran-2(3H)-one.

Intermediate 8: 3-((4-aminophenyl)(methyl)amino)dihydrofuran-2(3H)-one

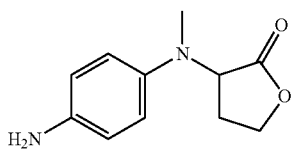

To a solution of tert-butyl (4-((2-oxotetrahydrofuran-3-yl)amino)phenyl)carbamate (1.5 g, 5.13 mmol) in DCM (30.0 mL) at 0° C. were added formaldehyde (37% in water, 1.2 mL, 16.4 mmol) and sodium triacetoxyborohydride (3.26 g, 15.39 mmol). The reaction mixture was stirred at 0° C. overnight and diluted in EtOAc. The organic layer was washed with sat NaHCO$_3$ (×3) and brine, dried over Na$_2$SO$_4$ and concentrated under vacuum. The residue was purified by flash chromatography (silica gel) eluting with pure DCM to give the expected compound tert-butyl (4-(methyl(2-oxotetrahydrofuran-3-yl)amino)phenyl)carbamate (1.3 g, 83%) as white powder.

To a solution of tert-butyl (4-(methyl(2-oxotetrahydrofuran-3-yl)amino)phenyl)carbamate (1.3 g, 4.24 mmol) in DCM (30 mL) was added TFA (4.29 mL, 55.7 mmol). The reaction mixture was stirred at room temperature overnight and concentrated under vacuum. The residue was diluted in a mixture MeCN/aq HCl (0.1 N) and freeze-dried to give the HCl salt of the intermediate 9 (644 mg, 54%) as white powder.

B.2. Compounds of the Invention

The compound of the invention may be prepared by methods well known to those skilled in the art and/or by adapting the methods described in WO2013/030365, WO2013/030366 and WO2013/030367.

In the table B.2.1 that is set forth below, exemplary compounds of the invention are described. In this table, the name of the compound, an arbitrarily assigned compound number and structural information are set out.

TABLE B.2.1

| Compounds of the invention | | |
|---|---|---|
| Name | # Cpd | Structure |
| 6-(aminomethyl)-$N^3$-(3-fluoropyridin-4-yl)-$N^{3'}$-(4-(((2-oxotetrahydrofuran-3-yl)amino)methyl)phenyl)-[1,1'-biphenyl]-3,3'-dicarboxamide | 1 | |
| 6-(aminomethyl)-$N^3$-(3-fluoropyridin-4-yl)-$N^{3'}$-(4-(((2-oxotetrahydrofuran-3-yl)methyl)thio)phenyl)-[1,1'-biphenyl]-3,3'-dicarboxamide | 2 | |
| 6-(aminomethyl)-$N^3$-(3-fluoropyridin-4-yl)-$N^{3'}$-(4-((2-oxotetrahydrofuran-3-yl)oxy)phenyl)-[1,1'-biphenyl]-3,3'-dicarboxamide | 3 | |

TABLE B.2.1-continued

Compounds of the invention

| Name | # Cpd | Structure |
|---|---|---|
| 6-(aminomethyl)-N-(3-fluoropyridin-4-yl)-3'-(N-((2-oxotetrahydrofuran-3-yl)thio)benzamido)-[1,1'-biphenyl]-3-carboxamide | 4 | 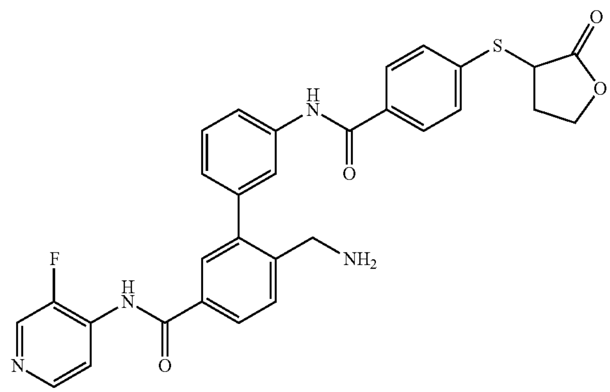 [SMILES: NCc1ccc(C(=O)Nc2ccncc2F)cc1-c1cccc(NC(=O)c2ccc(SC3CCOC3=O)cc2)c1] |
| 6-(aminomethyl)-N$^3$-(3-fluoropyridin-4-yl)-N$^{3'}$-(4-((2-oxotetrahydrofuran-3-yl)amino)phenyl)-[1,1'-biphenyl]-3,3'-dicarboxamide | 5 | 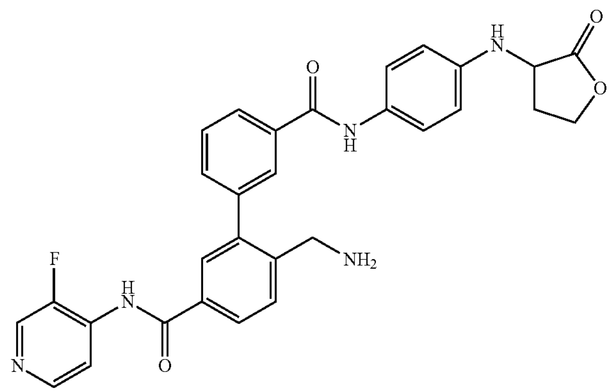 [SMILES: NCc1ccc(C(=O)Nc2ccncc2F)cc1-c1cccc(C(=O)Nc2ccc(NC3CCOC3=O)cc2)c1] |
| 6-(aminomethyl)-N$^3$-(3-fluoropyridin-4-yl)-N$^{3'}$-(4-((2-oxotetrahydrofuran-3-yl)thio)phenyl)-[1,1'-biphenyl]-3,3'-dicarboxamide | 6 | 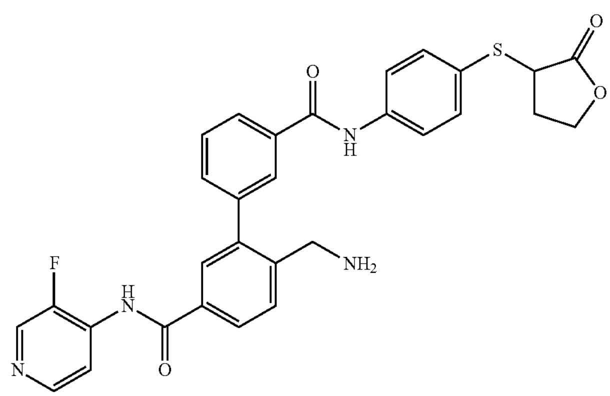 |
| 6-(aminomethyl)-N$^3$-(3-fluoropyridin-4-yl)-N$^{3'}$-(4-(methyl(2-oxotetrahydrofuran-3-yl)amino)phenyl)-[1,1'-biphenyl]-3,3'-dicarboxamide | 7 | 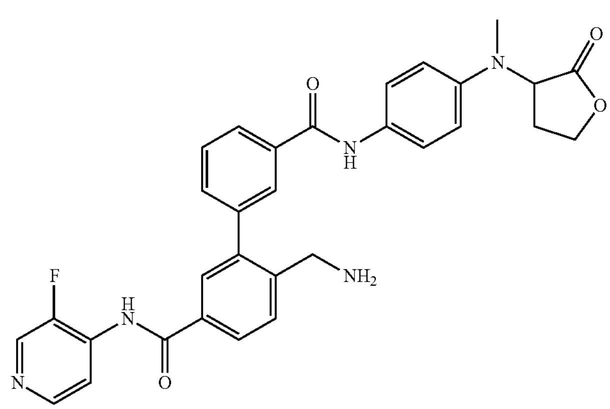 [SMILES: CN(c1ccc(NC(=O)c2cccc(-c3cc(C(=O)Nc4ccncc4F)ccc3CN)c2)cc1)C1CCOC1=O] |

TABLE B.2.1-continued

Compounds of the invention

| Name | # Cpd | Structure |
|---|---|---|
| 6-(aminomethyl)-N$^3$-(3-fluoropyridin-4-yl)-N$^{3'}$-(3-((2-oxotetrahydrofuran-3-yl)thio)phenyl)-[1,1'-biphenyl]-3,3'-dicarboxamide | 8 | 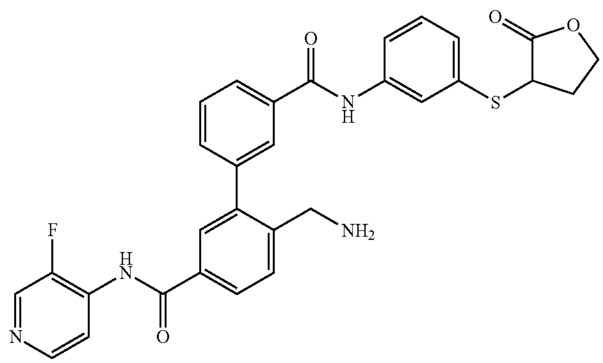 [SMILES: NCc1ccc(C(=O)Nc2ccncc2F)cc1-c1cccc(C(=O)Nc2cccc(SC3CCOC3=O)c2)c1] |
| 6-(aminomethyl)-N$^3$-(3-fluoropyridin-4-yl)-N$^{3'}$-(4-((5-methyl-2-oxotetrahydrofuran-3-yl)thio)phenyl)-[1,1'-biphenyl]-3,3'-dicarboxamide | 9 | 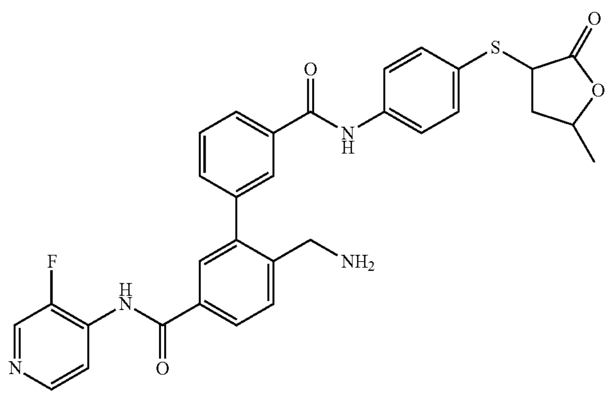 [SMILES: CC1CC(Sc2ccc(NC(=O)c3cccc(-c4cc(C(=O)Nc5ccncc5F)ccc4CN)c3)cc2)C(=O)O1] |
| 6-(aminomethyl)-N$^3$-(3-fluoropyridin-4-yl)-N$^{3'}$-(4-((4,4-dimethyl-2-oxotetrahydrofuran-3-yl)thio)phenyl)-[1,1'-biphenyl]-3,3'-dicarboxamide | 10 | 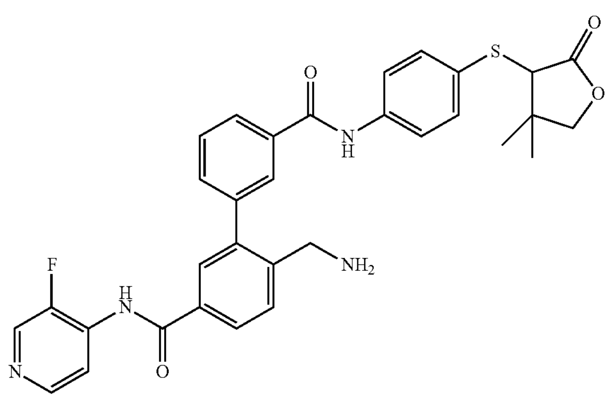 [SMILES: CC1(C)COC(=O)C1Sc1ccc(NC(=O)c2cccc(-c3cc(C(=O)Nc4ccncc4F)ccc3CN)c2)cc1] |
| 6-(aminomethyl)-N$^3$-(3-fluoropyridin-4-yl)-N$^{3'}$-(4-((2-oxotetrahydrofuran-4-yl)thio)phenyl)-[1,1'-biphenyl]-3,3'-dicarboxamide | 11 | 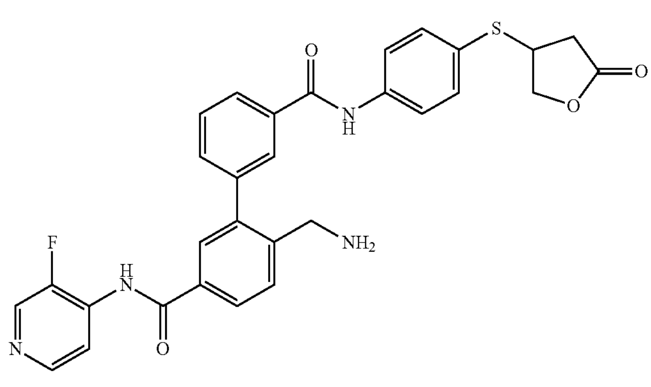 [SMILES: NCc1ccc(C(=O)Nc2ccncc2F)cc1-c1cccc(C(=O)Nc2ccc(SC3COC(=O)C3)cc2)c1] |

TABLE B.2.1-continued

Compounds of the invention

| Name | # Cpd | Structure |
|---|---|---|
| 6-(aminomethyl)-N$^3$-(3-fluoropyridin-4-yl)-N$^{3'}$-(2-fluoro-4-((2-oxotetrahydrofuran-3-yl)thio)phenyl)-[1,1'-biphenyl]-3,3'-dicarboxamide | 12 | 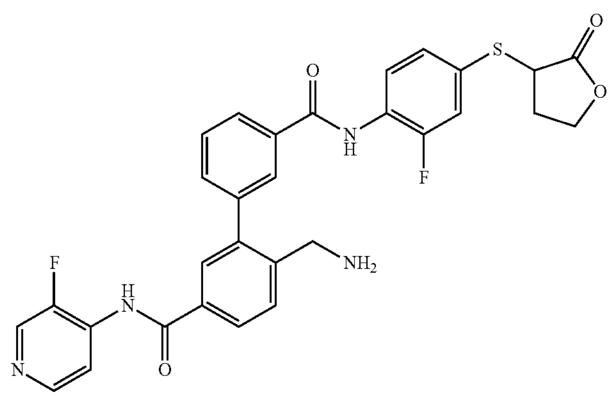 [SMILES: NCc1ccc(C(=O)Nc2ccncc2F)cc1-c1cccc(C(=O)Nc2ccc(SC3CCOC3=O)cc2F)c1] |
| 6-(aminomethyl)-N-(3-fluoropyridin-4-yl)-3'-(4-((2-oxotetrahydrofuran-3-yl)amino)benzamido)-[1,1'-biphenyl]-3-carboxamide | 13 | 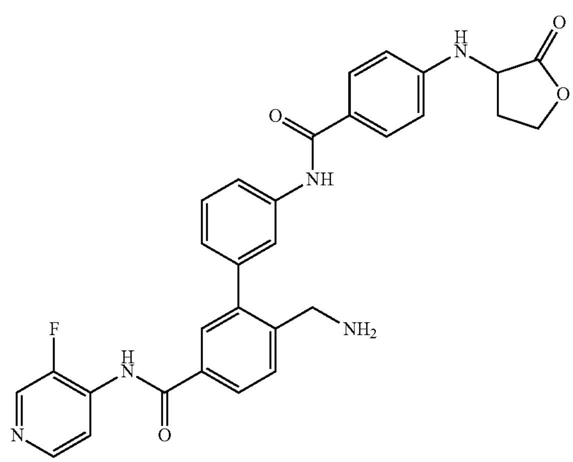 [SMILES: NCc1ccc(C(=O)Nc2ccncc2F)cc1-c1cccc(NC(=O)c2ccc(NC3CCOC3=O)cc2)c1] |
| 6-(aminomethyl)-N-(pyridin-4-yl)-3'-(4-((2-oxotetrahydrofuran-3-yl)thio)benzamido)-[1,1'-biphenyl]-3-carboxamide | 14 | 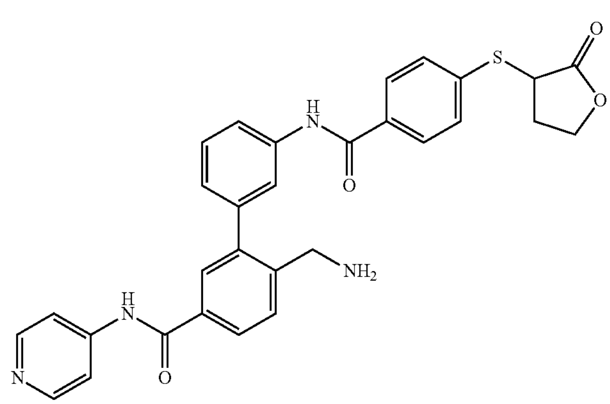 [SMILES: NCc1ccc(C(=O)Nc2ccncc2)cc1-c1cccc(NC(=O)c2ccc(SC3CCOC3=O)cc2)c1] |

TABLE B.2.1-continued

Compounds of the invention

| Name | # Cpd | Structure |
|---|---|---|
| 6-(aminomethyl)-N$^3$-(3-fluoropyridin-4-yl)-N$^{3'}$-(2-methyl-4-((2-oxotetrahydrofuran-3-yl)amino)phenyl)-[1,1'-biphenyl]-3,3'-dicarboxamide | 15 | 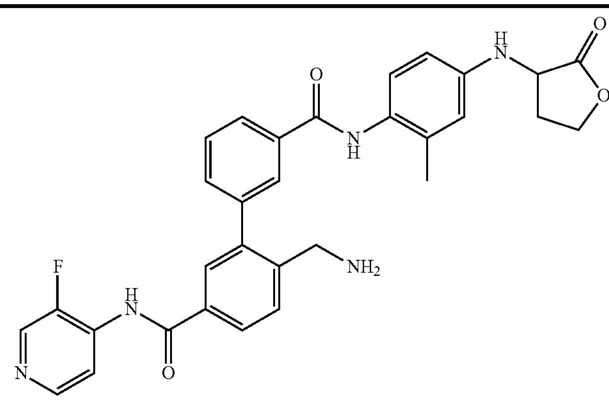 |
| 6-(aminomethyl)-N$^3$-(3-fluoropyridin-4-yl)-N$^{3'}$-(5-((2-oxotetrahydrofuran-3-yl)amino)thiazol-2-yl)-[1,1'-biphenyl]-3,3'-dicarboxamide | 16 | 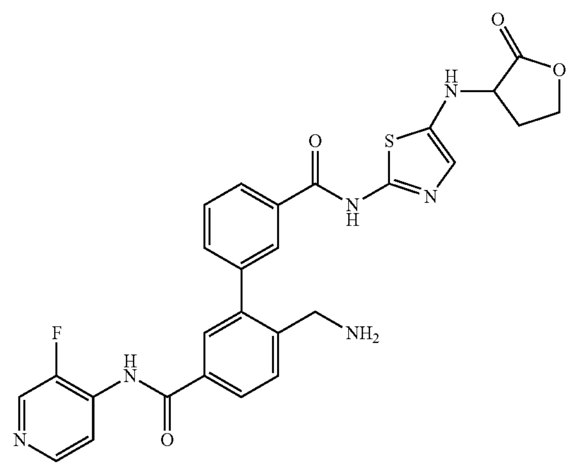 [SMILES: NCc1ccc(C(=O)Nc2ccncc2F)cc1-c1cccc(C(=O)Nc2ncc(NC3CCOC3=O)s2)c1] |

C. In Vitro and In Vivo Assays

C.1. ROCK Inhibitory Activity Screening

C.1.1. Kinase Inhibition

On-target activity against ROCK (1 or 2) ☐☐ was measured in a biochemical assay, using the following reagents: Base Reaction buffer; 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO. Required cofactors are added individually to each kinase reaction. The reaction procedure first involved the preparation of a peptide substrate in a freshly prepared reaction buffer. Required cofactors were then added to the substrate solution. ROCK (1 nM final concentration) was then delivered to the substrate solution. After gentle mix, DMSO solutions of the test compounds were added to the enzyme. Substrate mix $^{33}$P-ATP (specific activity 0.01 µCi/µl final) was then delivered into the reaction mixture to initiate the reaction. The kinase reaction was incubated for 120 min. at room temperature. Reactions were then spotted onto P81 ion exchange paper (Whatman # 3698-915). Filters were washed extensively in 0.1% Phosphoric acid. A radiometric count was then performed and IC$_{50}$ values were subsequently determined.

When evaluated under such conditions, compounds of the invention potently inhibit ROCK2 with an IC$_{50}$<100 nM.

C.1.2. MLC Phosphorylation Assay

Rat smooth muscle cell line A7r5 is used. The endogenous expression of ROCK results in a constitutive phosphorylation of the regulatory myosin light chain at T18/S19. A7r5 cells were plated in DMEM supplemented with 10% FCS in multiwall cell culture plates. After serum starvation overnight, cells were incubated with compounds in serum-free medium.

Quantification of MLC-T18/S19 phosphorylation is assessed in 96 well-plates via ELISA using a phspho-MLC-T18/S19 specific antibody and a secondary detection antibody. Raw data were converted into percent substrate phosphorylation relative to high controls, which were set to 100%. EC$_{50}$ values were determined using GraphPad Prism 5.01 software using a nonlinear regression curve fit with variable hill slope.

TABLE C.1.2

Activity data for MLC phosphorylation assay

| # Cpd | EC$_{50}$ MLC-PP |
|---|---|
| 1 | ++ |
| 2 | +++ |
| 3 | ++ |
| 4 | +++ |
| 5 | +++ |
| 6 | +++ |

TABLE C.1.2-continued

Activity data for MLC phosphorylation assay

| # Cpd | EC$_{50}$ MLC-PP |
|---|---|
| 7 | +++ |
| 8 | ++ |
| 9 | +++ |
| 11 | +++ |
| 12 | +++ |
| 13 | +++ |

++: 0.1 µM < EC$_{50}$ < 1 µM;
+++: EC$_{50}$ < 0.1 µM;

C.1.3. In Vivo Anti-Inflammatory Activity of Soft ROCK Inhibitors

Selected compounds of the invention were evaluated in vivo in an acute LPS lung challenge model. Groups of 6 male BALB/c mice were used for each tested dose and for positive and negative controls. Under anesthesia with gas anesthetics (isoflurane), test substances and vehicle (0.9% NaCl, 1 mL/kg) were administered intratracheally (IT) to test animals 0.5 hr prior to challenge with ~80 µg/kg of E. coli lipopolysaccharide (LPS, Sigma, serotype 055:B5, in sterile saline, 2 µg in 20 µL per mouse intratracheally). Dexamethasone, the positive control, at 1 mg/kg in 2% Tween 80 was given orally to test animals one hour before LPS challenge. Mice were anaesthetized with isoflurane at 24 hrs after LPS challenge, 0.5 mL of phosphate buffered saline (PBS, pH 7.4) was instilled into the lung twice through a tracheal cannula, after which about a total of 0.6~0.8 mL of bronchoalveolar lavage fluid (BALF) was obtained. Total cell and neutrophils counts in BALF were then determined and one-way ANOVA followed by Dunnett's test was used to analyze difference between the vehicle control and treated groups. Significant difference is considered at P<0.05. Compounds of the invention are efficacious in this model, with preferred compounds displaying an ED$_{50}$ below 0.5 mg/kg.

Example data is provided in FIG. 1 for Cpd4 that demonstrates, at 0.1 and 0.01 mg/kg, anti-inflammatory activity equivalent to the dexamethasone control.

C.2. Pharmacological Characterization

C.2.1. Stability Assay in Human Plasma

Compounds are incubated at a concentration of 1 µM in human (or animal) plasma. Samples are taken at fixed time points and the remnant of compound is determined by LC-MS/MS after protein precipitation. Half life in table C.2.1 is expressed in minutes.

TABLE C.2.1

Half-life values in plasma

| # Cpd | t½ human plasma |
|---|---|
| 1 | <20 |
| 2 | <20 |
| 3 | <20 |
| 4 | <20 |
| 5 | <20 |
| 6 | <20 |
| 7 | <20 |
| 8 | <20 |
| 9 | <20 |
| 11 | <20 |
| 12 | <20 |
| 13 | <20 |

C.2.2. Stability Towards Drug Metabolizing Enzymes in Lung S9

A 1 µM solution of the ROCK inhibitors is incubated with a reaction mixture containing lung S9 (EDTA-free) as well as the cofactors NADPH, UDPGA, PAPS and GSH. Samples are collected at 0, 15, 30 and 60 minutes post incubation. Negative control samples incubated with ROCK inhibitors and S9 fraction in the absence of cofactors are run in parallel. By using LC-MS/MS analysis, the percent of ROCK compounds remaining at each time point, the metabolic half-life of the ROCK compounds (expressed in minutes in table C.2.2) and the metabolic half-life of the control compounds are determined.

TABLE C.2.2

Half-life values in lungS9

| # Cpd | t½ human lung S9 |
|---|---|
| 1 | >60 |
| 2 | >60 |
| 4 | >60 |
| 5 | >60 |
| 6 | >60 |
| 7 | >60 |
| 13 | >60 |

C.2.3. Stability Towards Intestinal Drug Metabolizing Enzymes

A 1 µM solution of the ROCK inhibitors is incubated with human intestinal tissue homogenate (final concentration: 40 mg/ml) Samples are collected at 0, 20 and 60 minutes post incubation. By using LC-MS/MS analysis, the percent of ROCK compounds remaining at each time point, the metabolic half-life of the ROCK compounds (expressed in minutes in table C.2.3) and the metabolic half-life of control compounds are determined.

TABLE C.2.3

Half-life values in presence of 40 mg/ml intestinal homogenate.

| # Cpd | t½ (min) human | t½ (min) mouse |
|---|---|---|
| 2 | >120 | >120 |
| 5 | NT | >120 |
| 7 | >120 | >120 |

What is claimed is:

1. A method of treatment of fibrosis, wherein the method comprises administering to a patient in need thereof, a therapeutically effective amount of a compound of Formula I or a stereoisomer, tautomer, racemic, salt, hydrate, or solvate thereof,

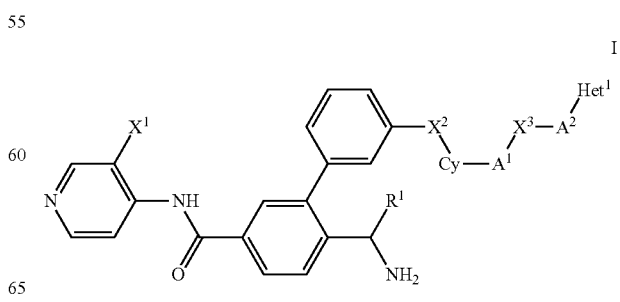

Wherein $R^1$ is selected from hydrogen and $C_{1-20}$alkyl;

$X^1$ is hydrogen or halo;

$X^2$ is —C(=O)—NH— or —NH—C(=O)—;

Cy is an optionally substituted group selected from aryl and heteroaryl;

$X^3$ is selected from the group consisting of —S—, —O—, and —NR$^2$—;

$R^2$ is hydrogen or $C_{1-6}$alkyl;

Het$^1$ is 2-oxotetrahydrofuranyl optionally substituted with one or more $C_{1-6}$alkyl-; and $A^1$ and $A^2$ are each independently a direct bond or an optionally substituted $C_{1-6}$alkylene.

2. The method of treatment according to claim 1, wherein Cy is selected from aryl and heteroaryl, wherein said aryl or heteroaryl is optionally substituted with one or more substituents selected from the group consisting of halo, hydroxyl, oxo, carbonyl, amino, amido, cyano, aryl, heteroaryl, $C_{3-8}$cycloalykl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$alkoxy, halo-$C_{1-8}$alkyl, thiol, $C_{1-8}$alkylthio, carboxylic acid, acylamino, $C_{1-8}$alkyl ester, carbamate, thioamido, urea, and sulfonamide.

3. The method of treatment according to claim 1, wherein Cy is aryl, wherein said aryl is optionally substituted with one or more substituents selected from the group consisting of halo, hydroxyl, oxo, carbonyl, amino, amido, cyano, aryl, heteroaryl, $C_{3-8}$cycloalkyl, $C_{3-8}$heterocyclyl, $C_{1-8}$alkylamino, $C_{1-8}$alkyl, di($C_{1-8}$alkyl)amino, $C_{1-8}$alkoxy, halo-$C_{1-8}$alkoxy, halo-$C_{1-8}$alkyl, thiol, $C_{1-8}$alkylthio, carboxylic acid, acylamino, $C_{1-8}$alkyl ester, carbamate, thioamido, urea and sulfonamide.

4. The method of treatment according to claim 1, wherein $A^1$ and $A^2$ are independently a direct bond or $C_{1-6}$alkylene, wherein said $C_{1-6}$alkylene is optionally substituted with one or more substituents selected from the group consisting of $C_{1-6}$alkyl, $C_{1-6}$alkenyl, $C_{1-6}$alkynyl, halo, hydroxyl, oxo, amino, cyano, aryl, heteroaryl, cycloalkyl, alkylamino, alkoxy, alkylthio, acylamino, carbamate, urea and sulfonamido.

5. The method of treatment according to claim 1, wherein:

$R^1$ is hydrogen;

$X^1$ is halo;

$X^2$ is —C(=O)—NH— or —NH—C(=O)—;

Cy is an optionally substituted group selected from aryl and heteroaryl;

$X^3$ is selected from the group consisting of —S—, —O—, and —NR$^2$—;

$R^2$ is hydrogen or methyl;

Het$^1$ is selected from the group consisting of

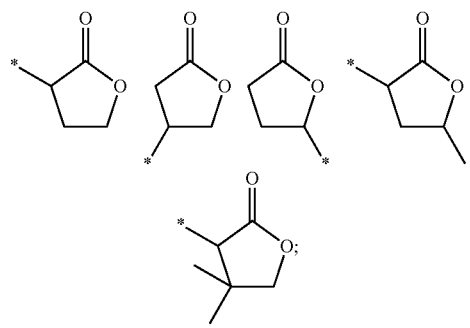

and $A^1$ and $A^2$ are each independently a direct bond or an optionally substituted $C_{1-6}$alkylene.

6. The method of treatment according to claim 1, wherein $A^1$ and $A^2$ are each independently a direct bond or a $C_{1-6}$alkylene, wherein said $C_{1-6}$alkylene is optionally substituted with one or more $C_{1-6}$alkyl groups.

7. A method of treatment as defined in claim 1, wherein the fibrosis is intestinal fibroisis.

* * * * *